(12) United States Patent
Abood et al.

(10) Patent No.: US 7,041,314 B2
(45) Date of Patent: May 9, 2006

(54) GPE ANALOGS AND PEPTIDOMINETICS

(75) Inventors: Norman A. Abood, Illinois, IL (US); Margaret Anne Brimble, Auckland (NZ)

(73) Assignee: Neuren Pharmaceuticals Ltd., Grafton (NZ)

( * ) Notice: Subject to any disclaimer, the term of this patent is extended or adjusted under 35 U.S.C. 154(b) by 0 days.

(21) Appl. No.: 10/155,864

(22) Filed: May 24, 2002

(65) Prior Publication Data

US 2003/0055004 A1 Mar. 20, 2003

Related U.S. Application Data

(60) Provisional application No. 60/293,853, filed on May 24, 2001.

(51) Int. Cl.
*A61K 31/401* (2006.01)
*C07D 207/16* (2006.01)

(52) U.S. Cl. .................. 424/451; 548/537; 424/464; 514/423

(58) Field of Classification Search ............ 548/537; 514/423; 424/451, 464
See application file for complete search history.

(56) References Cited

U.S. PATENT DOCUMENTS

| | | | |
|---|---|---|---|
| 4,444,879 A | 4/1984 | Foster et al. | |
| 4,511,390 A | 4/1985 | Kauer et al. | |
| 4,699,875 A | 10/1987 | Appel et al. | |
| 4,783,524 A | 11/1988 | Larsen et al. | |
| 4,906,614 A | 3/1990 | Giertz et al. | |
| 5,068,224 A | 11/1991 | Fryklund et al. | |
| 5,089,406 A | 2/1992 | Williams et al. | |
| 5,093,317 A | 3/1992 | Lewis et al. | 514/12 |
| 5,106,832 A | 4/1992 | Froesch et al. | |
| 5,114,840 A | 5/1992 | Tryggvason et al. | |
| 5,149,657 A | 9/1992 | Maugh et al. | |
| 5,243,038 A | 9/1993 | Ferrari et al. | |
| 5,273,961 A | 12/1993 | Clark et al. | |
| 5,420,112 A | 5/1995 | Lewis et al. | |
| 5,451,660 A | 9/1995 | Builder et al. | |
| 5,496,712 A | 3/1996 | Cappello et al. | |
| 5,635,604 A | 6/1997 | Dalboge et al. | |
| 5,639,729 A | 6/1997 | Goldstein et al. | |
| 5,648,335 A | 7/1997 | Lewis et al. | |
| 5,670,616 A | 9/1997 | Weber | |
| 5,679,552 A | 10/1997 | Dalboge et al. | |
| 5,686,423 A | 11/1997 | Wang et al. | |
| 5,691,169 A | 11/1997 | Dalboge et al. | |
| 5,703,045 A | 12/1997 | Lewis et al. | |
| 5,710,252 A | 1/1998 | Weber et al. | |
| 5,714,460 A | 2/1998 | Gluckman et al. | |
| 5,750,376 A | 5/1998 | Weiss et al. | |
| 5,801,045 A | 9/1998 | Weber et al. | |
| 5,804,550 A | 9/1998 | Bourguignon et al. | |
| 5,804,563 A | 9/1998 | Still et al. | |
| 5,861,373 A | 1/1999 | Gluckman et al. | |
| 5,965,531 A | 10/1999 | Webster et al. | 514/12 |
| 6,054,579 A | 4/2000 | Harriman | 540/200 |
| 6,187,906 B1 | 2/2001 | Gluckman et al. | 530/331 |
| 6,294,585 B1 | 9/2001 | Brown | |
| 6,342,585 B1 | 1/2002 | Grossman | |
| 6,365,573 B1 | 4/2002 | Gluckman et al. | 514/18 |
| 6,444,657 B1 | 9/2002 | Slusher et al. | |
| 6,682,753 B1 | 1/2004 | Alexi | 424/422 |
| 2001/0018199 A1 | 8/2001 | Dalboge et al. | |
| 2002/0013277 A1 | 1/2002 | Gluckman et al. | |
| 2002/0035066 A1* | 3/2002 | Gluckman et al. | 514/18 |
| 2002/0115594 A1 | 8/2002 | Bourguignon | |
| 2002/0151522 A1* | 10/2002 | Alexi | 514/54 |
| 2002/0177239 A1 | 11/2002 | Guan et al. | |
| 2003/0027755 A1 | 2/2003 | Guan et al. | |
| 2003/0105072 A1* | 6/2003 | Degenhardt et al. | 514/210.17 |
| 2003/0211990 A1 | 11/2003 | Sieg et al. | |

FOREIGN PATENT DOCUMENTS

| | | |
|---|---|---|
| EP | 227619 | 1/1987 |
| EP | 289314 | 2/1988 |
| EP | 308386 | 3/1989 |
| EP | 366638 | 5/1990 |
| EP | 357240 | 1/1993 |
| EP | 1043027 | 11/2000 |
| FR | 2707170 | 1/1995 |
| WO | WO 88/03533 | 5/1988 |
| WO | WO 88/08848 | 11/1988 |
| WO | WO 88/09171 | 12/1988 |
| WO | WO 89/01343 | 2/1989 |
| WO | WO 89/05822 | 6/1989 |
| WO | WO 90/05177 | 5/1990 |
| WO | WO 92/09695 | 6/1992 |
| WO | WO 93/02695 | 2/1993 |
| WO | WO 93/08826 | 5/1993 |
| WO | WO 93/08828 | 5/1993 |
| WO | WO 93/10806 | 6/1993 |

(Continued)

OTHER PUBLICATIONS

J. Neel, Pure and Applied Chemistry (1972), 31(1-2), 201-25.*
Carl Axel Bauer, European Journal of Biochemistry (1980), 105(3), 565-70.*
Blasio et al., Biopolymers (1993), 33 (4), 621-31.*

(Continued)

*Primary Examiner*—Kamal A. Saeed
*Assistant Examiner*—Rebecca Anderson
(74) *Attorney, Agent, or Firm*—Fliesler Meyer LLP

(57) ABSTRACT

This invention relates to analogs and peptidomimetics of glycyl-L-prolyl-L-glutamic acid (GPE). In particular, this invention relates to GPE analogs and peptidomimetics that are anti-apoptotic and anti-necrotic, to methods of making them, to pharmaceutical compositions containing them, and to their use.

16 Claims, 15 Drawing Sheets

FOREIGN PATENT DOCUMENTS

| WO | WO 93/20836 | 10/1993 |
| --- | --- | --- |
| WO | WO 93/21216 | 10/1993 |
| WO | WO 94/23754 | 10/1994 |
| WO | WO 94/26301 | 11/1994 |
| WO | PCT/NZ 94/00143 | 12/1994 |
| WO | WO 95/13823 | 5/1995 |
| WO | WO 95/17204 | 6/1995 |
| WO | WO 97/17090 | 5/1997 |
| WO | WO 97/39032 | 10/1997 |
| WO | WO 97/47735 | 12/1997 |
| WO | WO 98/14202 | 4/1998 |
| WO | WO 98/52620 | 11/1998 |
| WO | WO98/52620 | * 11/1998 |
| WO | WO 99/08702 | 2/1999 |
| WO | WO 99/15192 | 4/1999 |
| WO | WO 99/39210 | 8/1999 |
| WO | WO 99/65509 | 12/1999 |
| WO | WO 00/13650 | 3/2000 |
| WO | WO 02/16408 | 2/2002 |
| WO | WO 02/076208 A1 | 10/2002 |
| WO | WO 02/94856 | 11/2002 |

OTHER PUBLICATIONS

Challis et al., Journal of the Chemical Society, Perkin Transactions 1: Organic and Bio-Organic Chemistry (1990), (11), 3103-8.*

Hanusch-Kompa. et al., *Multi-Component Reactions 13: Synthesis of γ-Lactams as Part of a Multi-Ring System via Ugi-4-Centre-3-Component Reactions*. Tetrahedron Letters. 39 (1998) pp. 2725-2728.

Weinstein B., "Chemistry and Biochemistry of Amino Acids, Peptides and Proteins" vol. 7, 1983, pp. 266-357, XP002032461, Chapter 5, Arno F. Spatola.

Lucas, M.D., D. R., et. al., "The Toxic Effect of Sodium $_L$-Glutamate on the Inner Layers of the Retina", *Archives of Opthamology*, 58, 1957, pp. 198-204.

Curtis, David R., et al., "Amino Acid Transmitters in the Mammalian Central Nervous System", *Ergebnisse der Physiologie*, 69, 1974, pp. 97-188.

Bauer, Carl-Axel, "Active Centers of α-Chymotrypsin and of *Streptomyces griseus* Proteases 1 and 3," Department of Biochemistry, University of Lund, Nov. 5, 1979, pp. 565-570.

Carone, R.A. et al., "Differences Between *in vitro* and *in vivo* Degradation of LHRH by Rat Brain and Other Organs," *American Journal of Physiology*, 253, 1987, E317-E321.

Szabo, Laszlo, et. al., "The Bovine Insulin-like Growth Factor (IGF) Binding Protein Purified from Conditioned Medium Requires the N-Terminal Tripeptide in IGF-1 for Binding," *Biochemical and Biophysical Research Communications*, vol. 151, No. 1, Feb. 29, 1988, pp. 207-214.

Shepard, M.D., Gordon M., "Neurotransmitters and Neuromodulators," *Neurobiology*, 2$^{nd}$ edition, 1988, pp. 145-176.

Sakaki, Atsushi, et al., "Multiple Forms of Immunoreactive Growth Hormone-Releasing Hormone in Human Plasma, Hypothalamus, and Tumor Tissues," *Journal of Clinical Endocrinology and Metabolism*, vol. 68, No. 1, 1989, pp. 180-185.

Bourguignon, Jean-Pierre, et. al., "Pulsatile Release of Gonadortropin-Releasing Hormone from Hypothalamic Explants is Restrained by Blockade of N-Methyl-$_{D,L}$-Aspartate Receptors," *Endocrinology*, vol. 125, No. 2, 1989, pp. 1090-1096.

Sara, Vicki R., et. al., "Identification of Gly-Pro-Glu (GPE), the Aminoterminal Tripeptide of Insulin-like Growth Factor 1 Which is Truncated in Brain, as a Novel Neuroactive Peptide," *Biochemical and Biophysical Research Communications*, vol. 165, No. 2, Dec. 15, 1989, pp. 766-771.

Donoso, Alfredo O., et. al., "Glutamate Receptors of the Non-N-Methyl-$_D$-Aspartic Acid Type Mediate the Increase in Luteinizing Hormone-Releasing Hormone Release by Excitatory Amino Acids *in Vitro*", *Endocrinology*, vol. 126, No. 1, 1990, pp. 414-420.

Bourguignon, Jean-Pierre, et. al., "Maturation of the Hypothalamic Control of Pulsatile Gonadotropin-Releasing Hormone Secretion at Onset of Puberty: II. Reduced Potency of an Inhibitory Autofeedback," *Endocrinology*, vol. 127, No. 6, 1990, pp. 2884-2890.

Challis, Brian C., et al., "Synthesis and Characterisation of Some New N-Nitrosodipeptides," J. Chemistry Society Perkin Trans., 1990, pp. 3103-3108.

Sara, Vicki R., et al., "Neuroactive Products of IGF-1 and IGF-2 Gene Expression in the CNS," *Molecular Biology and Physiology of Insulin and Insulin-Like Growth Factors*, New York, 1991, pp. 439-448.

Hiney, Jill K., et al., "Insulin-Like Growth Factor I: A Possible Metabolic Signal Involved in the Regulation of Female Puberty," *Neuroendocrinology*, 54, 1991, pp. 420-423.

Bourguignon, Jean-Pierre, et. al., "Gonadal-Independent Developmental Changes in Activation of N-Methyl-D-Aspartate Receptors Involved in Gonadotropin-Releasing Hormone Secretion," *Neuroendocrinology*, 55, 1992, pp. 634-641.

Guan, Jian, et. al., "The Effects of IGF-1 Treatment After Hypoxic-Ischemic Brain Injury in Adult Rats," *J Cereb Blood Flow Metab*, vol. 13, No. 4, 1993, pp. 609-616.

Nilsson-Hakansson, Lena, et al., "The Effects of 1GF-1, Truncated IGF-1 and the Tripeptide Gly-Pro-Glu on Acetylcholine Release from Parietal Cortex of Rat Brain," *NeuroReport*, vol. 4, No. 9, Aug. 6, 1993, pp. 1111-1114.

Di Blasio,B., et al. "β-Alanine Containing Peptides: γ-Turns in Cyclotetrapeptides," Research Center on Bioactive Peptides, Napoli, Italy, *Biopolymers*, vol. 33, 1993, pp. 621-631.

Sara, Vicki R., et. al., "The Biological Role of Truncated Insulin-like Growth Factor-1 and the Tripeptide GPE in the Central Nervous System," *Annals of the New York Academy of Sciences*, 692, 1993, pp. 183-191.

Bourguignon, Jean-Pierre et. al., "Gonadotropin Releasing Hormone Inhibitory Autofeedback by Subproducts Antagonist at N-Methly-D-Aspartate Receptors: A Model of Autocrine Regulation of Peptide Scretion," The Endocrine Society, vol. 134, No. 3, 1994, pp. 1589-1592. The Endocrine Society, vol. 132, No. 3, 1994, pp. 1589-1592.

Saura, J. et al., "Neuroprotective Effects of Gly-Pro-Glu, the N-terminal Tripeptide of IGF-1, in the Hippocampus *in vitro*," *NeuroReport*, vol. 10, No. 1, Jan. 1999, pp. 161-164.

Néel, J., "Experimental Study of the Influence of Specific Intramolecular Interactions on the Conformation of Model Molecules (Peptides and Oligopetides)," Lagoratoire de Chimie-Physique Macromolecular, pp. 201-225.

Hanusch-Kompa and Ivar Ugi, "Multi-Component Reactions 13: Synthesis of γ-Lactams as Part of a Multi-Ring System Via Ugi-4-Centre-3-Component Reaction," Technische Universität München, Tetrahedron Letters 39, 1998, pp. 2725-2728.

* cited by examiner

FIG. 1
SYNTHETIC ANALOGUES OF GPE
I. MODIFY GLYCINE RESIDUE
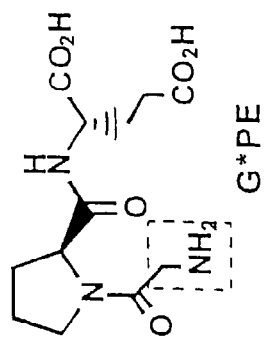
G*PE
II. MODIFY GLUTAMIC ACID RESIDUE
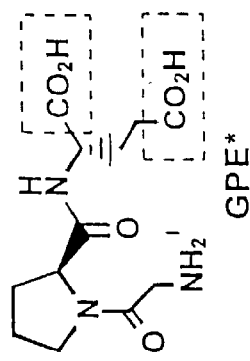
GPE*
i. α-carboxylic acid residue
ii. γ-carboxylic acid residue
iii. GPE diesters
III. MODIFY PEPTIDE LINKAGES
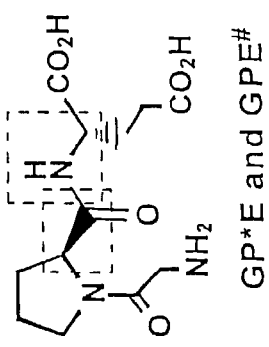
GP*E and GPE#
i. modify Pro - α-methylproline
ii. modify Glu - N-Methylglutamic acid
    α-Methylglutamic acid

FIG. 2 MODIFY GLYCINE RESIDUE

FIG. 3
MODIFY GLYCINE RESIDUE
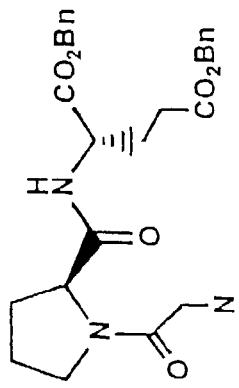
*Similarly:*
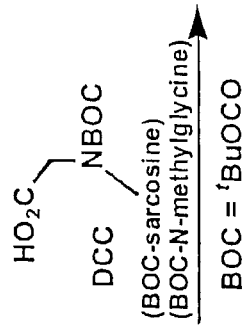
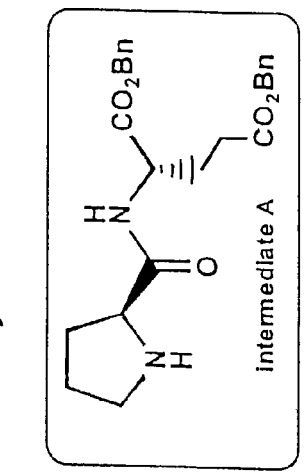
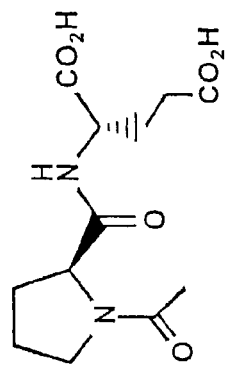
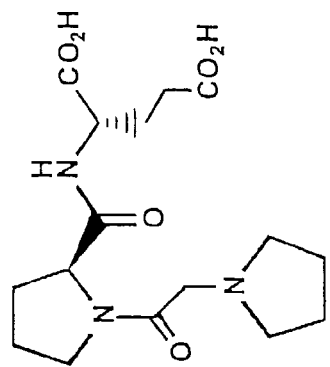
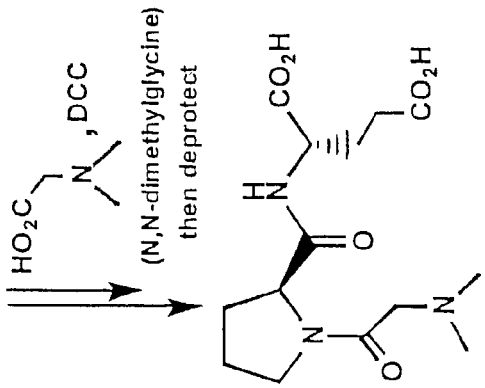

MODIFY GLUTAMIC ACID RESIDUE

*α-carboxylic acid - modify to an alkyl group*

FIG. 5
MODIFY GLUTAMIC ACID RESIDUE
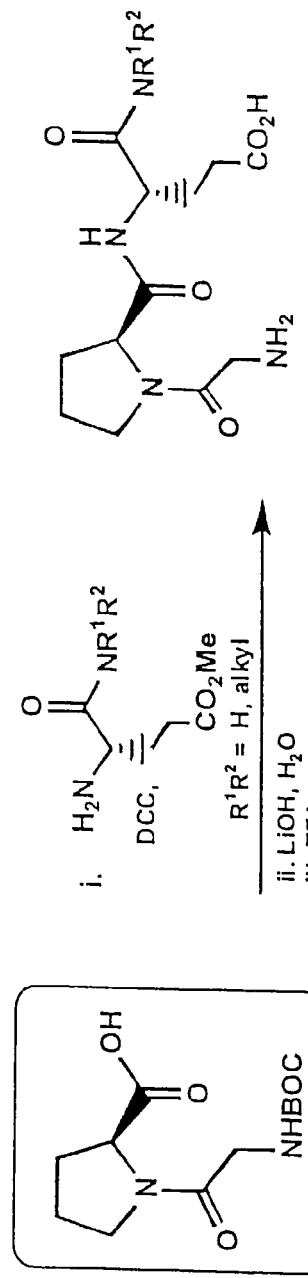
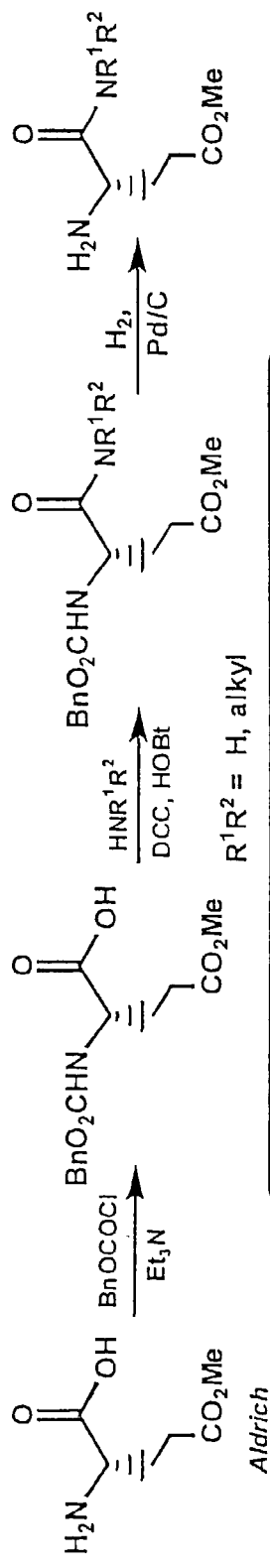

MODIFY GLUTAMIC ACID RESIDUE reduce γ-carboxylic acid - lactone prodrug

MODIFY GLUTAMIC ACID RESIDUE

*γ-carboxylic acid - modify to an alkyl group*

FIG. 8
MODIFY GLUTAMIC ACID RESIDUE
γ-carboxylic acid - modify to an amide
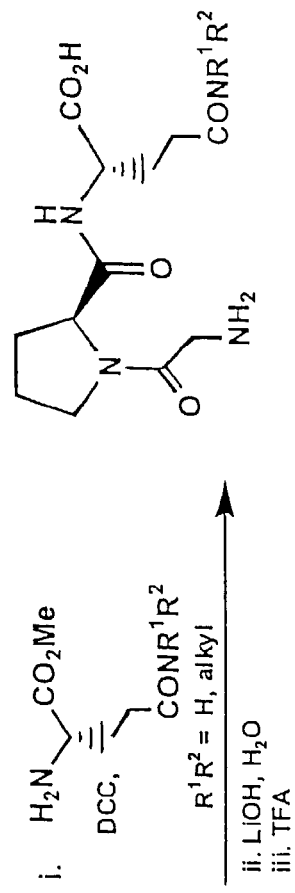
synthesis of amide
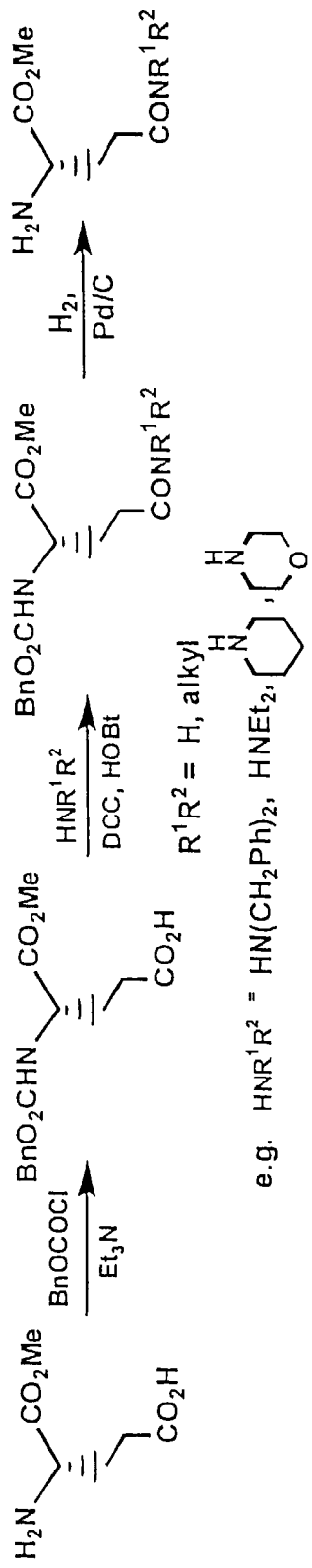

MODIFY GLUTAMIC ACID RESIDUE

*reduce γ-carboxylic acid - lactone prodrug*

MODIFY PEPTIDE LINKAGES (S)-α-methylproline

α-methylproline see: Seebach et al., Org. Synth., 1995, 72, 62.

FIG. 11
MODIFY PEPTIDE LINKAGES
*(S)-α-methylglutamic acid*
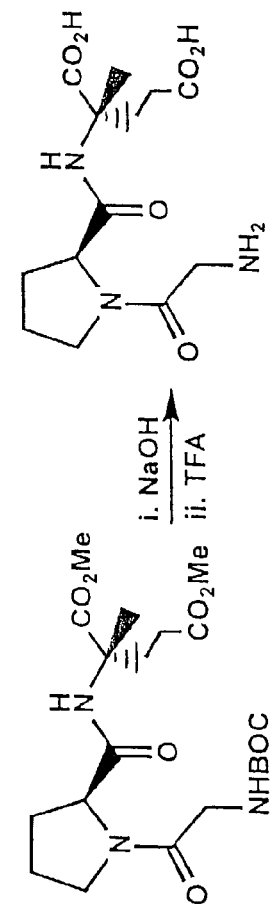
*N-methylglutamic acid*
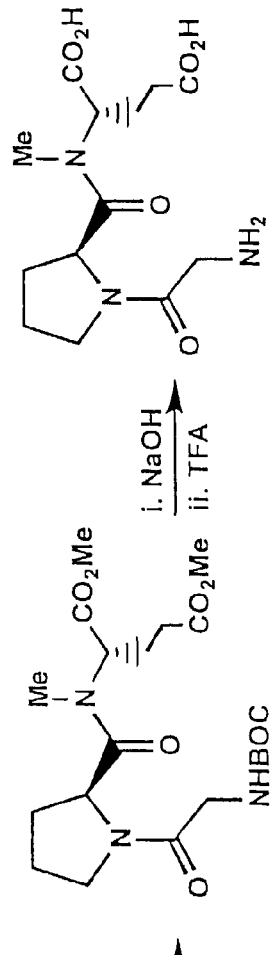

GPE ANALOGS AND PEPTIDOMINETICS

CROSS-REFERENCE TO RELATED APPLICATION

This application claims the priority under 35 USC 119(e) of U.S. Provisional Application No. 60/293,853, filed May 24, 2001, which is incorporated by reference into this application.

FIELD OF THE INVENTION

This invention relates to analogs and peptidomimetics of glycyl-L-prolyl-L-glutamic acid (GPE). In particular, this invention relates to GPE analogs and peptidomimetics that are anti-apoptotic and anti-necrotic, to methods of making them, to pharmaceutical compositions containing them, and to their use.

BACKGROUND

EP 0 366 638 discloses GPE (a tri-peptide consisting of the amino acids Gly-Pro-Glu) and its di-peptide derivatives Gly-Pro and Pro-Glu. EP 0 366 638 discloses that GPE is effective as a neuromodulator and is able to affect the electrical properties of neurons.

WO95/172904 discloses that GPE has neuroprotective properties and that administration of GPE can reduce damage to the central nervous system (CNS) by the prevention or inhibition of neuronal and glial cell death.

WO 98/14202 discloses that administration of GPE can increase the effective amount of choline acetyltransferase (ChAT), glutamic acid decarboxylase (GAD), and nitric oxide synthase (NOS) in the central nervous system (CNS).

WO99/65509 discloses that increasing the effective amount of GPE in the CNS, such as by administration of GPE, can increase the effective amount of tyrosine hydroxylase (TH) in the CNS for increasing TH-mediated dopamine production in the treatment of diseases such as Parkinson's disease. WO02/16408 discloses GPE analogs capable of inducing a physiological effect equivalent to GPE within a patient. The applications of the GPE analogs include the treatment of acute brain injury and neurodegenerative diseases, including but not limited to, injury or disease in the CNS.

The disclosures of these and other documents referred to in this application (including in the Figures) are incorporated herein by reference.

SUMMARY OF INVENTION

In its first aspect, this invention provides compounds of Formula 1 and Formula 2: where:

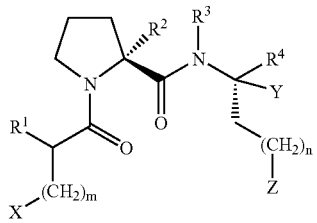

Formula 1

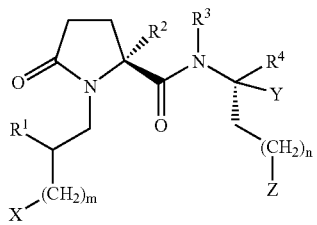

Formula 2 m is 0 or 1;
n is 0 or 1;
X is H or —$NR^6R^7$;
Y is H, alkyl, —$CO_2R^5$, or —$CONR^6R^7$;
Z is H, alkyl, —$CO_2R^5$ or —$CONR^6R^7$;
$R^1$ is H, alky, or aralkyl;
$R^2$, $R^3$, and $R^4$ are independently H or alkyl;
each $R^5$ is independently H, alkyl, or a fatty alcohol residue;
each $R^6$ and $R^7$ is independently H, alkyl, or aralkyl, or —$NR^6R^7$ is pyrrolidino, piperidino, or morpholino;
and a lactone formed when a compound where Y is —$CO_2$(alkyl) and Z is —$CO_2H$ or where Y is —$CO_2H$ and Z is —$CO_2$(alkyl) is lactonized;
and the pharmaceutically acceptable salts thereof,
provided that the compound is not GPE, N-Me-GPE, GPE amide, APE, GPQ or a salt thereof.

In a second aspect, this invention provides pharmaceutical compositions comprising a pharmaceutically acceptable excipient and a therapeutically effective amount of at least one compound of this invention. These compositions find use as anti-apoptotic and anti-necrotic agents, and for conditions where administration of a GPE analog or peptidomimetic is indicated.

In a third aspect, this invention provides a method of treating an animal having a disease or injury capable of treatment by administration of a GPE analog or peptidomimetic, comprising administration to that animal of at least one compound of this invention, optionally in conjunction with at least one other conventional therapeutic agent for the disease being treated.

In a fourth aspect, this invention provides methods of preparing the compounds of the first aspect of this invention.

BRIEF DESCRIPTION OF THE DRAWINGS

FIG. 1 is a general scheme for preparation of compounds of the invention.

FIGS. 2 and 3 are schemes for the modification of the glycine residue within compounds of the invention.

FIGS. 4 through 9 are schemes for the modification of the glutamic acid residue within compounds of the invention.

FIGS. 10 and 11 are schemes for the modification of peptide linkages within compounds of the invention.

DETAILED DESCRIPTION OF THE DRAWINGS

Definitions

Figure 2:
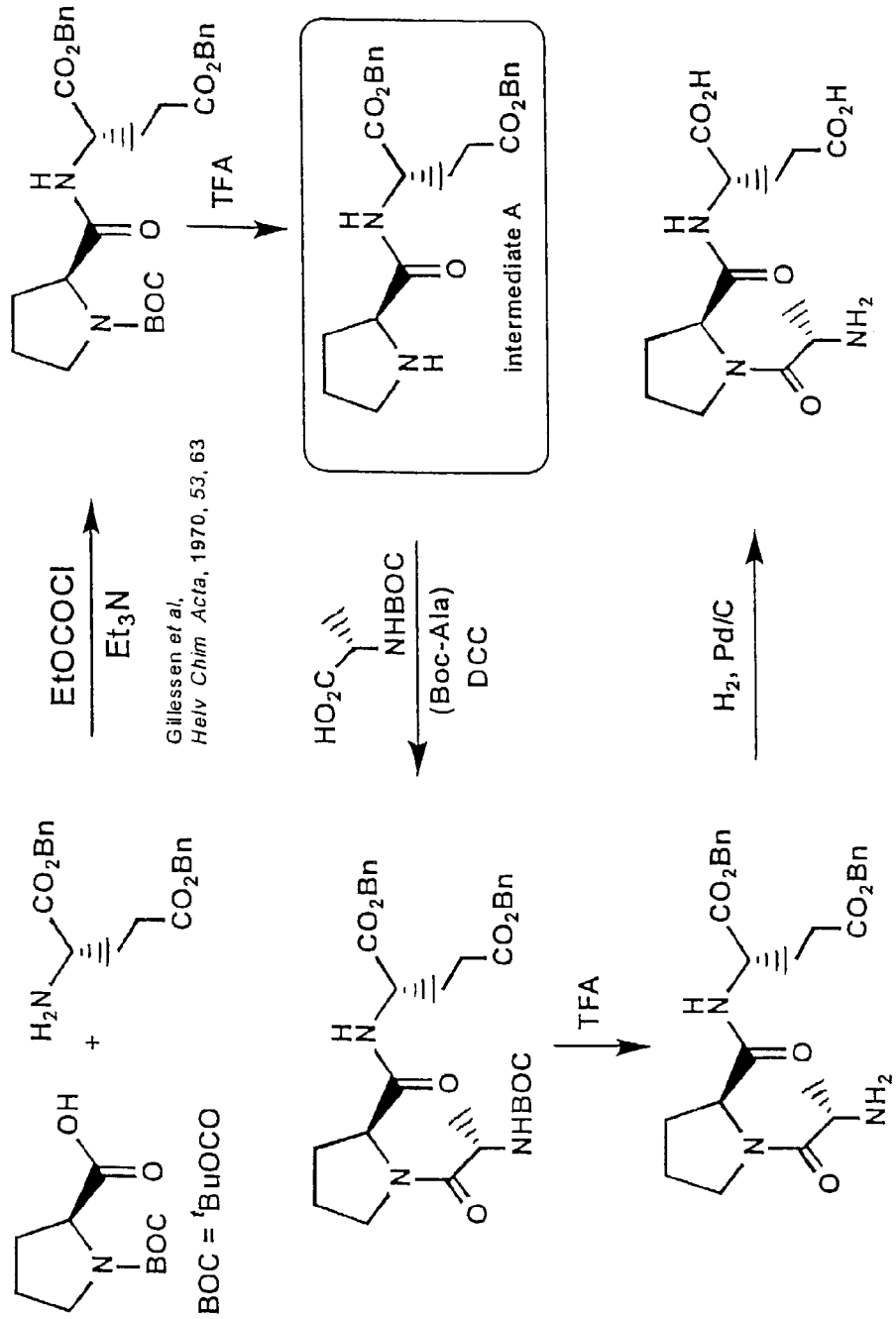

"Alkyl" means a linear saturated hydrocarbyl group having from one to six carbon atoms, or a branched or cyclic saturated hydrocarbyl group having from three to six carbon atoms. Examplary alkyl groups include methyl, ethyl, isopropyl, cyclopropyl, tert-butyl, cyclopropylmethyl, and hexyl.

"Animal" includes humans and non-human mammals, such as domestic animals (cats, dogs, and the like) and farm animals (cattle, horses, sheep, goats, swine, and the like).

"Aralkyl" means a group of the formula —$(CH_2)_{1-2}$Ar, where Ar is a 5- or 6-membered carbocyclic or heterocyclic aromatic ring, optionally substituted with 1 to 3 substituents selected from Cl, Br, —OH, —O-alkyl, —$CO_2R^8$ (where $R^8$ is H or alkyl), or —$NR^8R^9$, where $R^8$ is as described previously and $R^9$ is H or alkyl. Exemplary aralkyl groups include benzyl, 2-chlorobenzyl, 4-(dimethylamino)benzyl, phenethyl, 1-pyrrolylmethyl, 2-thienylmethyl, and 3-pyridylmethyl.

"Disease" includes any unhealthy condition of an animal including particularly Parkinson's disease, Huntington's disease, Alzheimer's disease, multiple sclerosis, diabetes, and cognitive dysfunction due to aging.

A "fatty alcohol residue" is a linear hydrocarbyl group having from seven to twenty carbon atoms, optionally containing up to three carbon-carbon double bonds. Exemplary fatty alcohol residues include decyl, pentadecyl, hexadecyl (cetyl), octadecyl (stearyl), oleyl, linoleyl, and eicosyl.

A "growth factor" means an extracellular polypeptide-signaling molecule that stimulates a cell to grow or proliferate.

"Injury" includes any acute damage of an animal including particularly non-hemorrhagic stroke, traumatic brain injury, perinatal asphyxia associated with fetal distress such as following abruption, cord occlusion or associated with intrauterine growth retardation, perinatal asphyxia associated with failure of adequate resuscitation or respiration, severe CNS insults associated with near miss drowning, near miss cot death, carbon monoxide inhalation, ammonia or other gaseous intoxication, cardiac arrest, coma, meningitis, hypoglycemia and status epilepticus, episodes of cerebral asphyxia associated with coronary bypass surgery, hypotensive episodes and hypertensive crises, and cerebral trauma.

A "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

A "pharmaceutically acceptable salt" means a salt that is pharmaceutically acceptable and has the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono—acid-mono-salt or a di-salt; and similarly where there are more than two acidic groups present, some or all of such groups can be salified.

A "protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete.

A "therapeutically effective amount" means the amount that, when administered to an animal for treating a disease, is sufficient to effect treatment for that disease.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease).

Implicit hydrogen atoms (such as the hydrogens on the pyrrolidine ring, etc.) are omitted from the formulae for clarity, but should be understood to be present.

Presently Preferred Compounds

While the broadest definition of the invention is set out in the Summary of the Invention, certain compounds of this invention are presently preferred.

Presently preferred compounds of this invention are compounds where:
(a) the compounds are compounds of Formula 1;
(b) m is 0;
(c) n is 1;
(d) at least one of X, Y, $R^1$, $R^2$, $R^3$, $R^4$ and $R^5$ is not hydrogen;
(e) X is —$NR^6R^7$; and
(f) Y is —$CO_2R^5$ or —$CO_2NR^6R^7$; and
(g) Z is —$CO_2R^5$ or —$CO_2NR^6R^7$.

Particularly preferred compounds of the invention are compounds of Formula I wherein X is —$NR^6R^7$ and $R^6$ and $R^7$ are independently alkyl or aralkyl. The more preferred embodiment is a compound of Formula I wherein X is —$NR^6R^7$ and both $R^6$ and $R^7$ are alkyl.

A number of different preferences have been given above, and following any one of these preferences results in a compound of this invention that is more presently preferred than a compound in which that particular preference is not followed. However, these preferences are generally independent, and additive; and following more than one of these preferences may result in a more presently preferred compound than one in which fewer preferences are followed.

Pharmacology and Utility

The compounds of this invention are anti-apoptotic and anti-necrotic. Their anti-apoptotic and anti-necrotic activity in vivo can be measured by cell counts, by methods such as those discussed in Klempt N D et al: Hypoxia-ischemia induces transforming growth factor β1 mRNA in the infant rat brain. Molecular Brain Research: 13: 93–101. Their activity can also be measured in vitro. The compounds of this invention are also expected to have pharmacological properties and therapeutic activities similar to those of GPE, and these activities may be measured by the methods known in the art, and discussed in the documents cited herein, for measuring the activity of GPE.

The therapeutic ratio of a compound can be determined, for example, by comparing the dose that gives effective anti-apoptotic and anti-necrotic activity in a suitable in vivo model such as a hypoxic-ischemic injury [Sirimanne E S, Guan J, Williams C E and Gluckman P D: Two models for determining the mechanisms of damage and repair after hypoxic-ischemic injury in the developing rat brain. Journal of Neuroscience Methods: 55: 7–14, 1994] in a suitable animal species such as the rat, with the dose that gives significant observable side-effects in the test animal species.

Pharmaceutical Compositions and Administration

In general, compounds of this invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease or injury, its severity, the age and relative health of the animal being treated, the potency of the compound(s), and other factors. As anti-apoptotic and anti-necrotic agents, therapeutically effective amounts of compounds of this invention may range from 0.001 to 1000 milligrams per kilogram (mg/Kg) mass of the animal, for example, 0.1 to 10 mg/Kg, with lower doses such as 0.001 to 0.1 mg/Kg, e.g. about 0.01 mg/Kg, being appropriate for administration through the cerebrospinal fluid, such as by intracerebroventricular administration, and higher doses such as 1 to 100 mg/Kg, e.g. about 10 mg/Kg, being appropriate for administration by methods such as oral, systemic (e.g. transdermal), or parenteral (e.g. intravenous) administration. A person of ordinary skill in the art will be able without undue experimentation, having regard to that skill and this disclosure, to determine a therapeutically effective amount of a compound of this invention for a given disease or injury.

In general, compounds of this invention will be administered as pharmaceutical compositions by one of the following routes: oral, topical, systemic (e.g. transdermal, intranasal, or by suppository), parenteral (e.g. intramuscular, subcutaneous, or intravenous injection), by administration to the CNS (e.g. by intraspinal or intracisternal injection); by implantation, and by infusion through such devices as osmotic pumps, transdermal patches, and the like. Compositions may take the form of tablets, pills, capsules, semi-solids, powders, sustained release formulation, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as Gennaro A R: Remington: The Science and Practice of Pharmacy, 20$^{th}$ ed., Lippincott, Williams & Wilkins, 2000. Suitable liquid carriers, especially for injectable solutions, include water, aqueous saline solution, aqueous dextrose solution, and the like, with isotonic solutions being preferred for intravenous, intraspinal, and intracisternal administration and vehicles such as artificial cerebrospinal fluid being also especially suitable for administration of the compound to the CNS.

Compounds of this invention are also suitably administered by a sustained-release system. Suitable examples of sustained-release compositions include semi-permeable polymer matrices in the form of shaped articles, e.g., films, or microcapsules. Sustained-release matrices include poly-lactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al., 1981), ethylene vinyl acetate (Langer et al., supra), or poly-D-(−)-3-hydroxybutyric acid (EP 133,988). Sustained-release compositions also include a liposomally entrapped compound. Liposomes containing the compound are prepared by methods known per se: DE 3,218,121; Epstein et al., 1985; Hwang et al., 1980; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mole percent cholesterol, the selected proportion being adjusted for the most efficacious therapy.

Compounds of this invention may also be PEGylated to increase their lifetime in vivo, based on, e.g., the conjugate technology described in WO 95/32003.

Desirably, if possible, when administered as anti-apoptotic and anti-necrotic agents, compounds of this invention will be administered orally. The amount of a compound of this invention in the composition may vary widely depending on the type of composition, size of a unit dosage, kind of excipients, and other factors well known to those of ordinary skill in the art. In general, the final composition may comprise from 0.0001 percent by weight (% w) to 10% w of the compound of this invention, preferably 0.001% w to 1% w, with the remainder being the excipient or excipients.

An anti-apoptotic and anti-necrotic composition may optionally contain, in addition to a compound of this invention, at least one anti-apoptotic agent selected from, for example, growth factors and associated derivatives (insulin-like growth factor-I [IGF-I], insulin-like growth factor-II [IGF-II], transforming growth factor-β1, activin, growth hormone, nerve growth factor, growth hormone binding protein, IGF-binding proteins [especially IGFBP-3], basic fibroblast growth factor, acidic fibroblast growth factor, the hst/Kfgk gene product, FGF-3, FGF-4, FGF-6, keratinocyte growth factor, androgen-induced growth factor. Additional members of the FGF family include, for example, int-2, fibroblast growth factor homologous factor-1 (FHF-1), FHF- 2, FHF-3 and FHF-4, keratinocyte growth factor 2, glial-activating factor, FGF-10 and FGF-16, ciliary neurotrophic factor, brain derived growth factor, neurotrophin 3, neurotrophin 4, bone morphogenetic protein 2 [BMP-2], glial-cell line derived neurotrophic factor, activity-dependant neurotrophic factor, cytokine leukaemia inhibiting factor, oncostatin M, interleukin), α-, β-, γ-, or consensus interferon, and TNF-α. Other forms of neuroprotective therapeutic agents include, for example, clomethiazole; kynurenic acid, Semax, tacrolimus, L-threo-1-phenyl-2-decanoylamino-3-morpholino-1-propanol, adrenocorticotropin-(4-9) analog [ORG 2766] and dizolcipine [MK-801], selegiline; glutamate antagonists such as, NPS1506, GV1505260, MK-801, GV150526; AMPA antagonists such as 2,3-dihydroxy-6-nitro-7-sulfamoylbenzo(f)quinoxaline (NBQX), LY303070 and LY300164; anti-inflammatory agents directed against the addressin MAdCAM-1 and/or its integrin α4 receptors (α4β1 and α4β7), such as anti-MAdCAM-1mAb MECA-367 (ATCC accession no. HB-9478). Most of these agents, especially the peptides such as the growth factors, etc. are not orally active, and will require administration by injection or infusion.

Preparation of the Compounds of this Invention

The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to the person of ordinary skill in the art following procedures described in such references as Fieser and Fieser's Reagents for Organic Synthesis, vols 1–17, John Wiley and Sons, New York, N.Y., 1991; Rodd's Chemistry of Carbon Compounds, vols. 1–5 and supplements, Elsevier Science Publishers, 1989; Organic Reactions, vols. 1–40, John Wiley and Sons, New York, N.Y., 1991; March J; Advanced Organic Chemistry, 4$^{th}$ ed. John Wiley and Sons, New York, N.Y., 1992; and Larock: Comprehensive Organic Transformations, VCH Publishers, 1989. In most instances, amino acids and their esters or amides, and protected amino acids, are widely commercially available; and the preparation of modified amino acids and their amides or esters are extensively described in the chemical and biochemical literature and thus well-known to persons of ordinary skill in the art. For example, N-pyrrolidineacetic acid is described in Dega-Szafran Z and Pryzbylak R. Synthesis, IR, and NMR studies of zwitterionic α-(1-pyrrolidine)alkanocarboxylic acids and their N-methyl derivatives. J. Mol. Struct.: 436–7, 107–121, 1997; and N-piperidineacetic acid is described in Matsuda O, Ito S, and Sekiya M. Reaction of N-(alkoxymethyl) dialkylamines and N,N'-methylenebisdialkylamines with isocyanides. Chem. Pharm. Bull.: 23(1), 219–221, 1975.

The starting materials, intermediates, and compounds of this invention may be isolated and purified using conventional techniques, including filtration, distillation, crystallization, chromatography, and the like. They may be characterized using conventional methods, including physical constants and spectral data.

Unless specified to the contrary, the reactions described herein take place at atmospheric pressure over a temperature range between about 0° C. and 125° C.

The compounds of this invention may be prepared by the methods described below and as given in the Example.

Compounds of Formula 1 are analogs of GPE, or modifications thereof, such as esters or amides. In general, they may be prepared by methods such as are already well-known to persons of ordinary skill in the art of peptide and modified peptide synthesis, following the reaction schemes set forth in the 11 Figures following this specification, or by following other methods well-known to those of ordinary skill in the art of the synthesis of peptides and analogs.

Conveniently, synthetic production of the polypeptide of the invention may be according to the solid phase synthetic method described by Merrifield et al. Solid phase peptide synthesis. I. The synthesis of a tetrapeptide: J. Amer. Chem. Soc. 85, 2149–2156, 1963. This technique is well understood and is a common method for preparation of peptides. The solid phase method of synthesis involves the stepwise addition of protected amino acids to a growing peptide chain which is bound by covalent bonds to a solid resin particle. By this procedure, reagents and by-products are removed by filtration, thus eliminating the necessity of purifying intermediates. The general concept of this method depends on attachment of the first amino acid of the chain to a solid polymer by a covalent bond. Succeeding protected amino acids are added, one at a time (stepwise strategy), or in blocks (segment strategy), until the desired sequence is assembled. Finally, the protected peptide is removed from the solid resin support and the protecting groups are cleaved off.

The amino acids may be attached to any suitable polymer as a resin. The resin must contain a functional group to which the first protected amino acid can be firmly linked by a covalent bond. Various polymers are suitable for this purpose, such as cellulose, polyvinyl alcohol, polymethylmethacrylate, and polystyrene. Suitable resins are commercially available and well known to those of skill in the art. Appropriate protective groups usable in such synthesis include tert-butyloxycarbonyl (BOC), benzyl (Bzl), t-amyloxycarbonyl (Aoc), tosyl (Tos), o-bromo-phenylmethoxycarbonyl (BrZ), 2,6-dichlorobenzyl (BzlCl$_2$), and phenylmethoxycarbonyl (Z or CBZ). Additional protective groups are identified in Merrifield, cited above, as well as in McOmie J F W: Protective Groups in Organic Chemistry, Plenum Press, New York, 1973.

The general procedure of preparation of the peptides of this invention involves initially attaching the protected carboxyl-terminal amino acid to the resin. After attachment the resin is filtered, washed and the protecting group (desirably BOC) on the I-amino group of the carboxyl-terminal amino acid is removed. The removal of this protecting group must take place, of course, without breaking the bond between that amino acid and the resin. The next amino, and if necessary, side chain protected amino acid, is then coupled to the free I-amino group of the amino acid on the resin. This coupling takes place by the formation of an amide bond between the free carboxyl group of the second amino acid and the amino group of the first amino acid attached to the resin. This sequence of events is repeated with successive amino acids until all amino acids are attached to the resin. Finally, the protected peptide is cleaved from the resin and the protecting groups removed to reveal the desired peptide.

The cleavage techniques used to separate the peptide from the resin and to remove the protecting groups depend upon the selection of resin and protecting groups and are known to those familiar with the art of peptide synthesis.

Alternative techniques for peptide synthesis are described in Bodanszky et al, Peptide Synthesis, 2nd ed, John Wiley and Sons, New York, 1976. For example, the peptides of the invention may also be synthesized using standard solution peptide synthesis methodologies, involving either stepwise or block coupling of amino acids or peptide fragments using chemical or enzymatic methods of amide bond formation. [See, e.g. H. D. Jakubke in The Peptides, Analysis, Synthesis, Biology, Academic Press, New York, 1987, p. 103–165; J. D. Glass, ibid., pp. 167–184; and European Patent 0324659 A2, describing enzymatic peptide synthesis methods.] These solution synthesis methods are well known in the art.

Commercial peptide synthesizers, such as the Applied Biosystems Model 430A, are available for the practice of these methods.

A person of ordinary skill in the art will have no difficulty, taking account of that skill and the knowledge available, and of this disclosure, in developing one or more suitable synthetic methods for compounds of this invention.

For example, analogs in which the glycine residue of GPE is replaced by an alternative amino acid, or by a non-amino acid, may conveniently be prepared by the preparation of a protected proline-glutamic acid di-peptide (such as the dibenzyl ester), and coupling that dipeptide with a protected glycine analog, such as BOC-N-methylglycine, BOC-L-valine, N-pyrrolidineacetic acid, and the like, followed by deprotection, as illustrated in FIGS. 2 and 3. Analogs in which the glutamic acid residue of GPE is replaced by an alternative amino acid or an amino acid amide or ester may conveniently be prepared by the preparation of a protected glycine-L-proline di-peptide (such as BOC-glycyl-L-proline), and coupling that dipeptide with a protected glutamic acid or analog thereof, such as tert-butyl γ-aminobutyrate, tert-butyl 4-methyl-4-aminopentanoate, tert-butyl 4-aminopentanoate, methyl 4-amino-4-dimethylcarbamoylbutyrate, L-glutamine methyl ester, dimethyl l-methyl-L-glutamate, etc. Lactones may be prepared by the preparation of an appropriate mono-acid-mono-ester derivative and reduction Analogs in which $R^2$ is alkyl may conveniently be prepared simply by use of the appropriate 2-alkylproline in the synthesis, and similarly analogs in which $R^3$ is alkyl may conveniently be prepared by the use of the appropriate N-alkylglutamic acid or analog in the synthesis. Where modifications are to be made to two or more amino acids, the coupling techniques will still be the same, with just more than one modified amino acid or analog being used in the synthesis. The choice of appropriate protecting groups for the method chosen (solid-phase or solution-phase), and of appropriate substrates if solid-phase synthesis is used, will be within the skill of a person of ordinary skill in the art.

Figure 4:
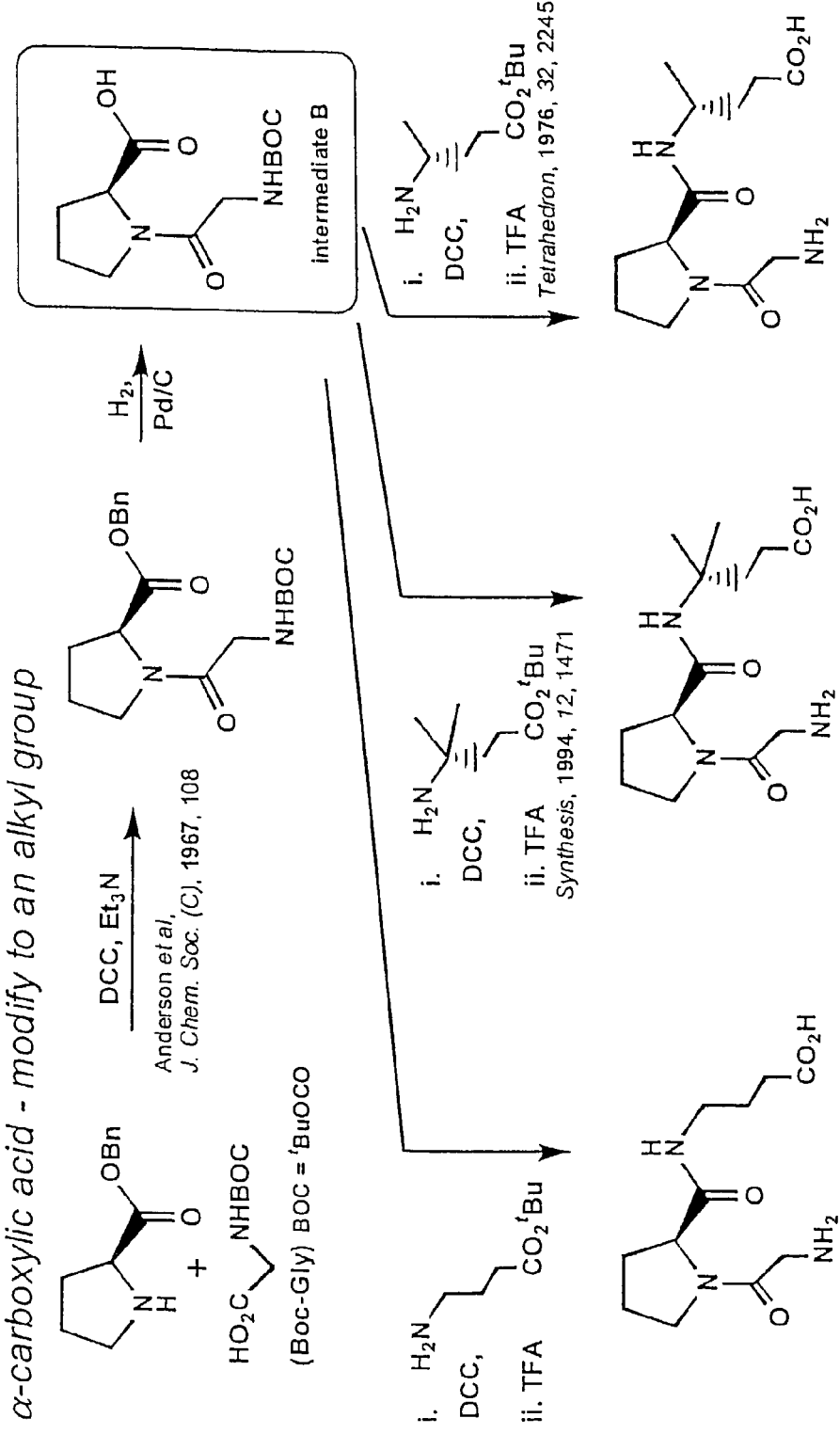
Figure 6:
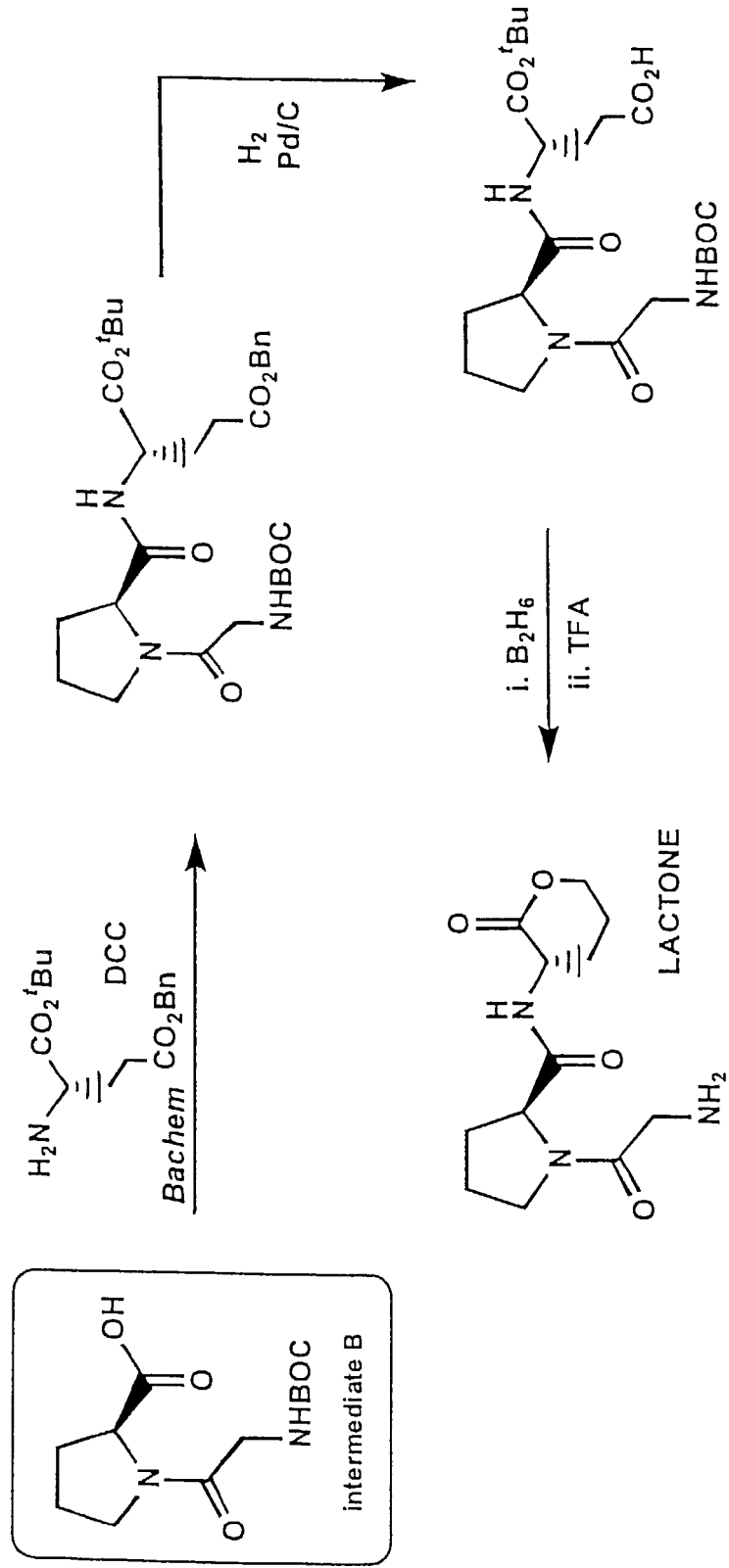
Figure 7:
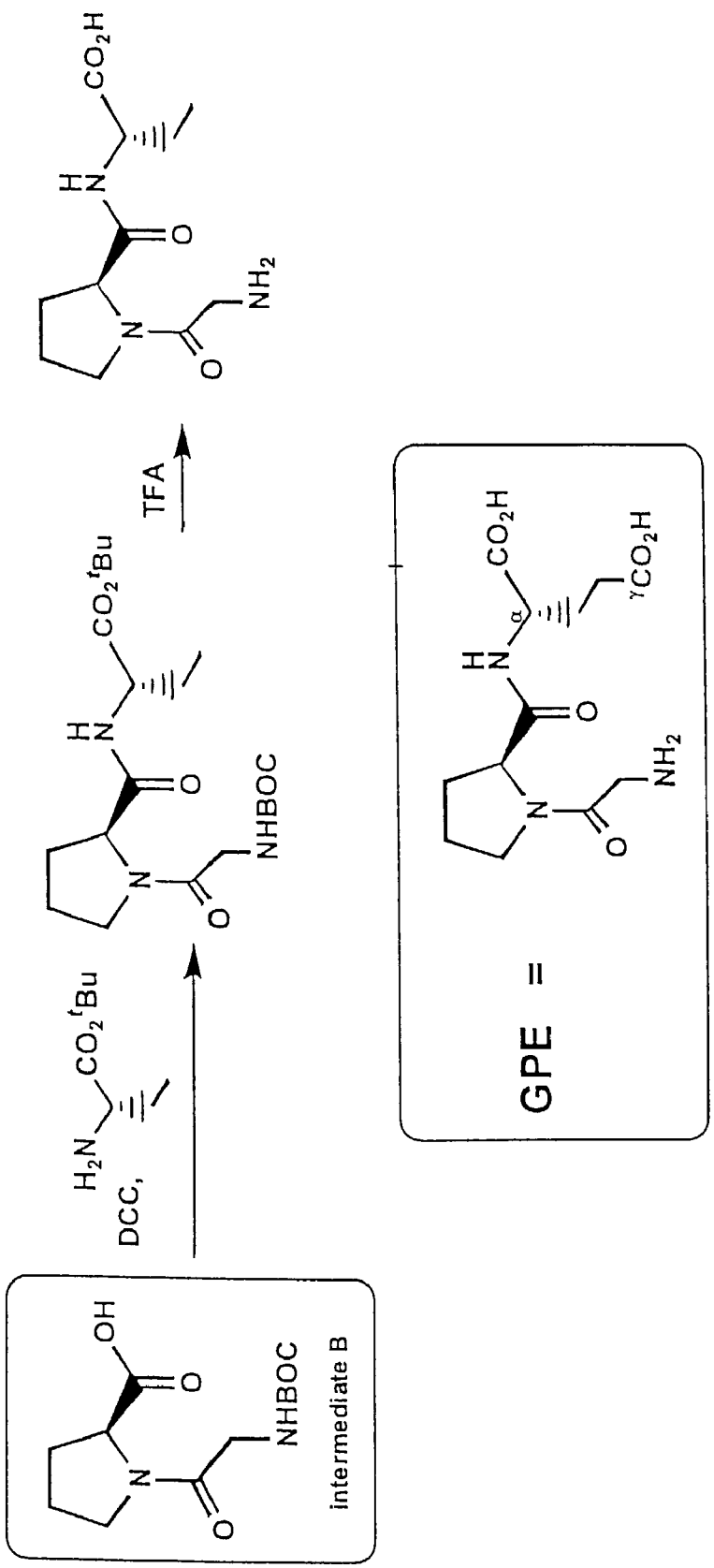
Figure 9:
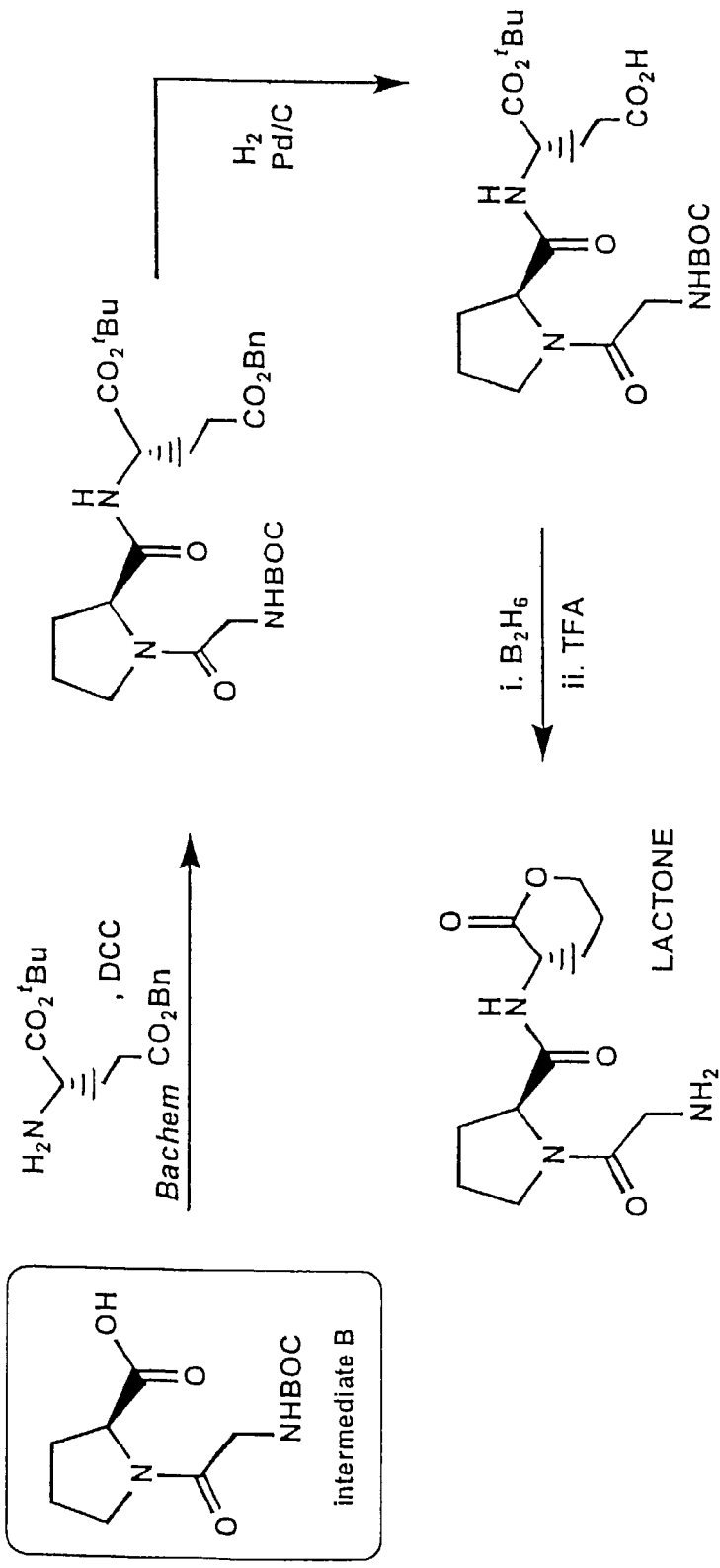
Figure 10:
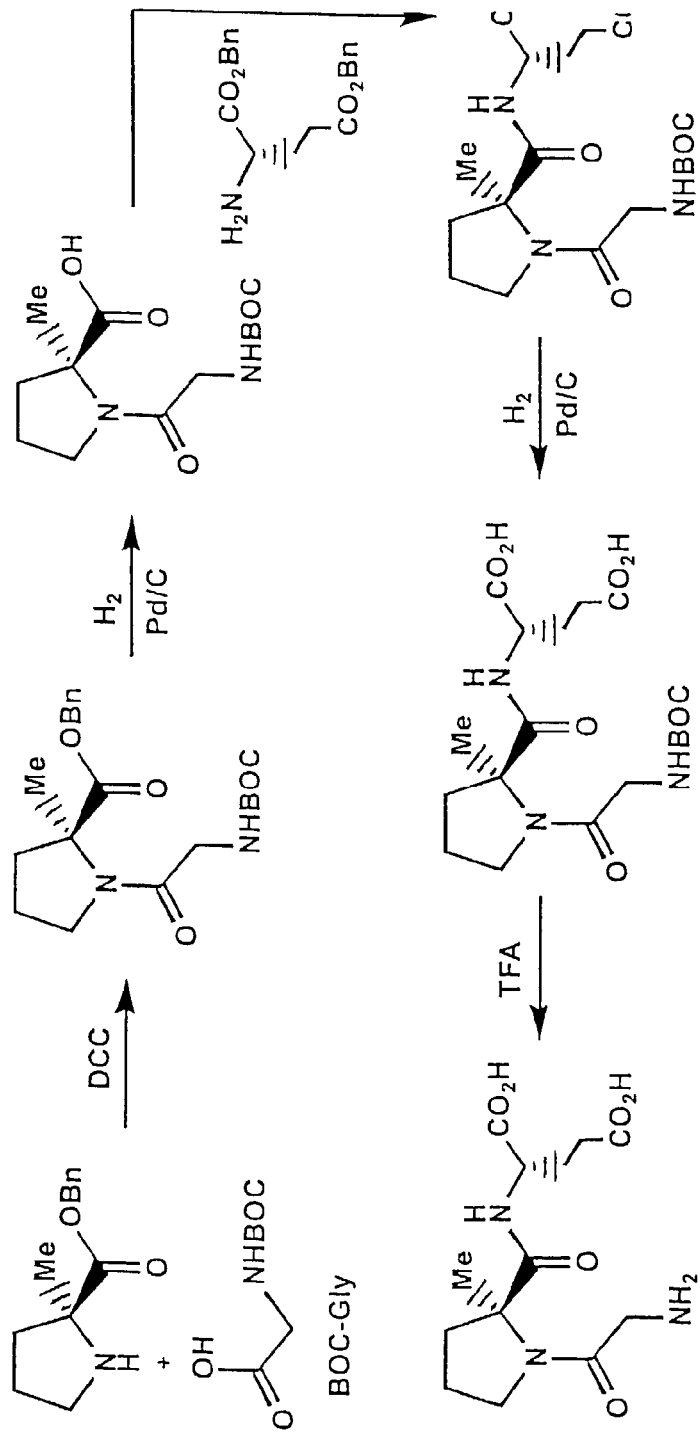
Figure 12:
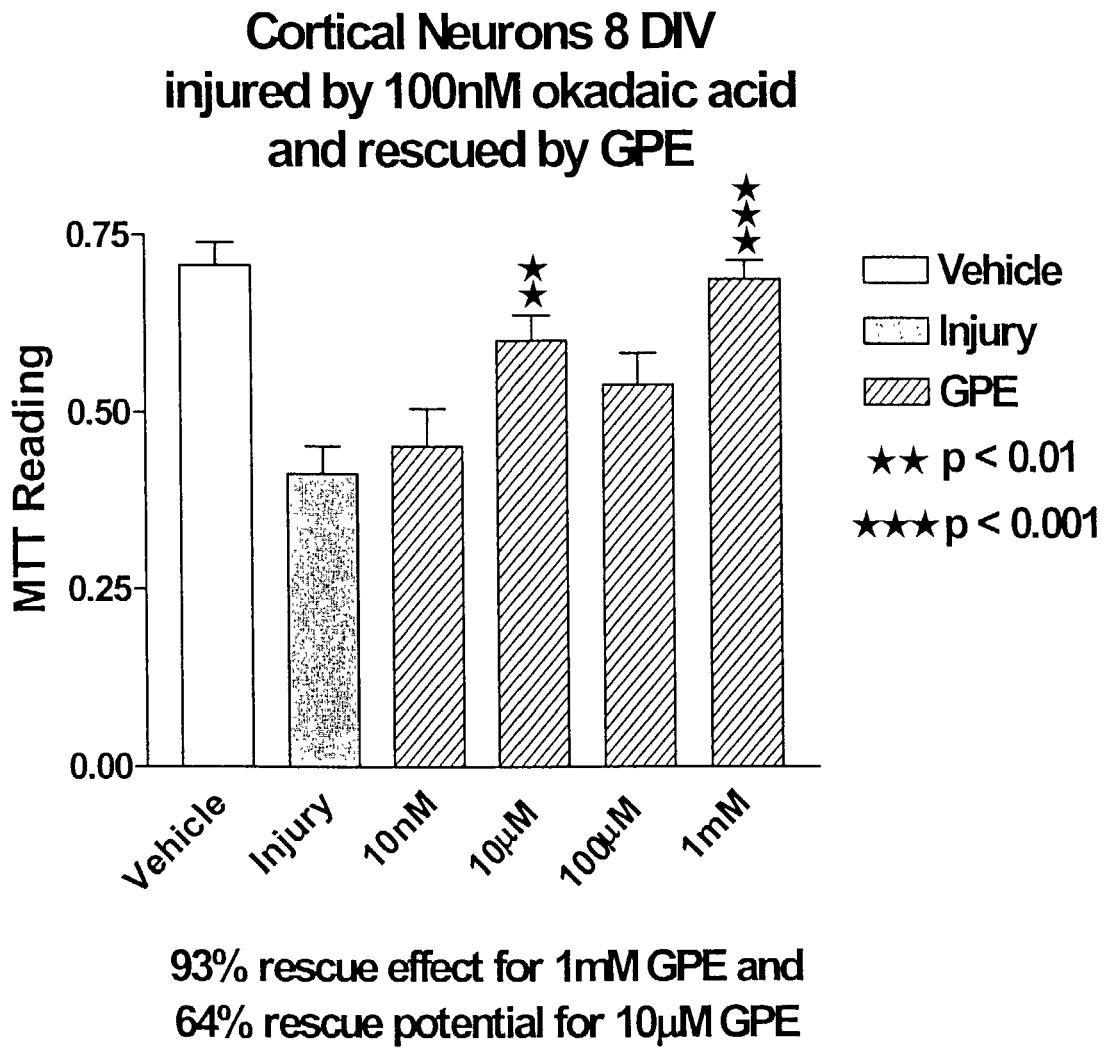
FIGS. 12–15 summarize the testing results.
Figure 13:
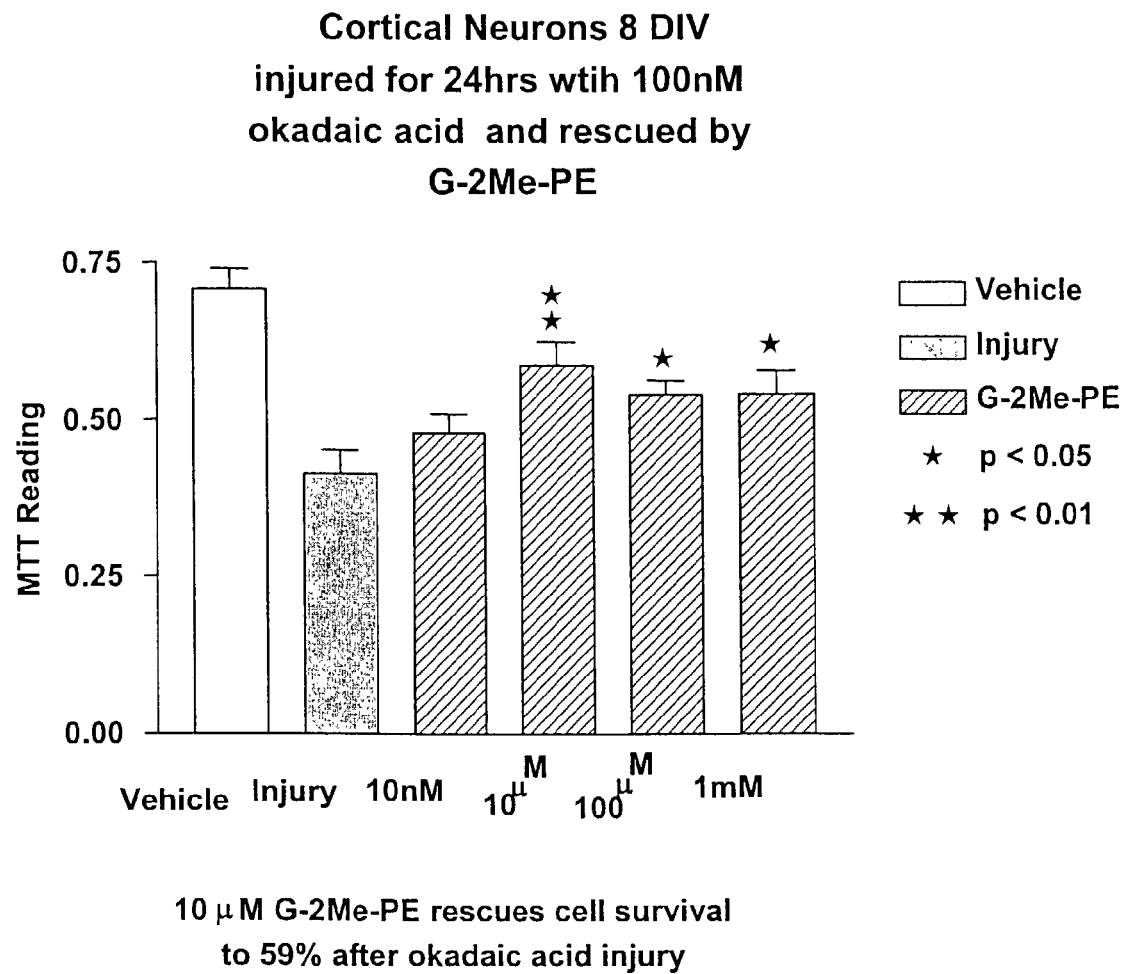

Compounds of Formula 2 may be prepared from suitably protected 5-oxo-L-proline or analogs or derivatives thereof, following methods such as the coupling of the proline carboxyl group with a protected glutamic acid or analog or derivative to give an analog of intermediate A of FIG. 2, comparable to the coupling reaction shown in FIG. 2, and then alkylating the pyrrolidine nitrogen with a group of the formula A—$(CH_2)_m$—$CH(R^1)$—$CH_2R$, protected at A if necessary, where R is a leaving group under alkylation conditions. Alternatively, the suitably protected 5-oxo-L-proline may first be alkylated at the pyrrolidine nitrogen to give an analog of intermediate B of FIG. 4, and then coupling this with a suitably protected glutamic acid or analog or derivative in the manner shown in FIGS. 4 through 9.

EXAMPLE

The following non-limiting example illustrates the synthesis of a compound of the invention, N,N-dimethylglycyl-L-prolyl-L-glutamic acid.

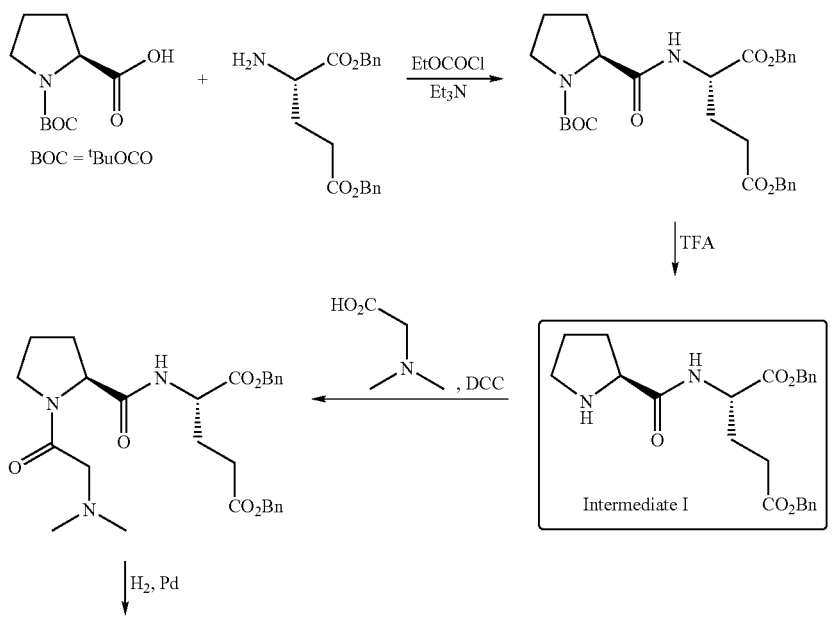

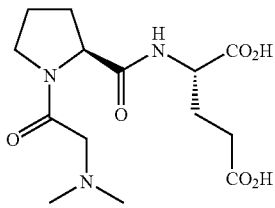

All starting materials and other reagents were purchased from Aldrich; BOC=tert-butoxycarbonyl; Bn=benzyl.

BOC-(γ-benzyl)-L-prolyl-L-glutamic acid benzyl ester

To a solution of BOC-proline [Anderson GW and McGregor AC: J. Amer. Chem. Soc.: 79, 6180, 1957] (10 mmol) in dichloromethane (50 ml), cooled to 0° C., was added triethylamine (1.39 ml, 10 mmol) and ethyl chloroformate (0.96 ml, 10 mmol). The resultant mixture was stirred at 0° C. for 30 minutes. A solution of dibenzyl L-glutamate (10 mmol) was then added and the mixture stirred at 0° C. for 2 hours then warmed to room temperature and stirred overnight. The reaction mixture was washed with aqueous sodium bicarbonate and citric acid (2 mol $l^{-1}$) then dried (MgSO$_4$) and concentrated at reduced pressure to give BOC-(γ-benzyl)-L-prolyl-L-glutamic acid dibenzyl ester (5.0 g, 95%).

(γ-Benzyl)-L-prolyl-L-glutamic acid dibenzyl ester

A solution of BOC-(γ-benzyl)-L-prolyl-L-glutamic acid dibenzyl ester (3.4 g, 10 mmol), cooled to 0° C., was treated with trifluoroacetic acid (25 ml) for 2 hr at room temperature. After removal of the volatiles at reduced pressure the residue was triturated with ether to give (γ-benzyl)-L-prolyl-L-glutamic acid dibenzyl ester (I).

N,N-Dimethylglycyl-L-prolyl-L-glutamic acid

A solution of dicyclohexylcarbodiimide (10.3 mmol) in dichloromethane (10 ml) was added to a stirred and cooled (0° C.) solution of (γ-benzyl)-L-prolyl-L-glutamic acid dibenzyl ester (10 mmol), N,N-dimethylglycine (10 mmol) and triethylamine (10.3 mmol) in dichloromethane (30 ml). The mixture was stirred at 0° C. overnight and then at room temperature for 3 h. After filtration, the filtrate was evaporated at reduced pressure. The resulting crude dibenzyl ester was dissolved in a mixture of ethyl acetate (30 ml) and methanol (30 ml) containing 10% palladium on charcoal (0.5 g) then hydrogenated at room temperature and pressure until the uptake of hydrogen ceased. The filtered solution was evaporated and the residue recrystallized from ethyl acetate to yield the tri-peptide derivative.

It will be evident that following the method of the Example, and using alternative amino acids or their amides or esters, will yield other compounds of Formula 1.

Testing: Material and Methods

The following experimental protocol followed guidelines approved by the University of Auckland animal ethics committee.

Preparation of cortical astrocyte cultures for harvest of metabolised cell culture supernatant One cortical hemisphere from a postnatal day 1 rat was used and collected into 4 ml of DMEM. Trituration was done with a 5 ml glass pipette and subsequently through an 18 gauge needle. Afterwards, the cell suspension was sieved through a 100 μm cell strainer and washed in 50 ml DMEM (centrifugation for 5 min at 250 g). The sediment was resuspended into 20 ml DMEM+10% fetal calf serum. 10 Milliliters of suspension was added into each of two 25 cm$^3$ flasks and cultivated at 37° C. in the presence of 10% CO$_2$, with a medium change twice weekly. After cells reached confluence, they were washed three times with PBS and adjusted to Neurobasal/B27 and incubated for another 3 days. This supernatant was frozen for transient storage until usage at −80° C.

Preparation of Striatal and Cortical Tissue from RAT E18/E19 Embryos

A dam was sacrificed by CO$_2$-treatment in a chamber for up to 4 minutes and was prepared then for cesarean section. After surgery, the embryos were removed from their amniotic sacs, decapitated and the heads put on ice in DMEM/F12 medium for striatum and PBS+0.65% D(+)-glucose for cortex.

Striatal Tissue Extraction Procedure and Preparation of Cells

Whole brain was removed from the skull with the ventral side facing upside in DMEM/F12 medium. The striatum was dissected out from both hemispheres under a stereomicroscope and the striatal tissue was placed into the Falcon tube on ice.

The collected striatal tissue was triturated by using a P1000 pipettor in 1 ml of volume. The tissue was triturated by gently pipetting the solution up and down into the pipette tip about 15 times, using shearing force on alternate outflows. The tissue pieces settled to the bottom of the Falcon tube within 30 seconds, subsequently the supernatant was transferred to a new sterile Falcon tube on ice. The supernatant contained a suspension of dissociated single cells. The tissue pieces underwent a second trituration to avoid excessively damaging cells already dissociated by over triturating them. 1 Milliliter of ice-cold DMEM/F12 medium was added to the tissue pieces in the first tube and triturated as before. The tissue pieces were allowed to settle and the supernatant was removed to a new sterile Falcon tube on ice. The cells were centrifuged at 250 g for 5 minutes at 4° C. The resuspended cell pellet was ready for cell counting.

Plating and Cultivation of Striatal Cells

Striatal cells were plated into Poly-L-Lysine (0.1 mg/ml) coated 96-well plates (the inner 60 wells only) at a density of 200,000 cells /cm$^2$ in Neurobasal/B27 medium (Invitrogen). The cells were cultivated in the presence of 5% CO$_2$ at 37° C. under 100% humidity. Complete medium was changed on days 1, 3 and 6.

Cortical Tissue Extraction Procedure and Preparation of Cells

The two cortical hemispheres were carefully removed by a spatula from the whole brain with the ventral side facing upside into a PBS +0.65% D(+)-glucose containing petri dish. Forcips were put into the rostral part (near B. olfactorius) of the cortex for fixing the tissue and two lateral—sagittal oriented cuttings were done to remove the paraform and entorhinal cortices. The next cut involved a frontal oriented cut at the posterior end to remove the hippocampal formation. A final frontal cut was done a few millimeters away from the last cut in order to get hold of area 17/18 of the visual cortex.

The collected cortices on ice in PBS+0.65% D(+)-glucose were centrifuged at 350 g for 5 min. The supernatant was removed and trypsin/EDTA (0.05%/0.53 mM) was added for 8 min at 37° C. The reaction was stopped by adding an equal amount of DMEM+10% fetal calf serum. The supernatant was removed by centrifugation followed by two subsequent washes in Neurobasal/B27 medium.

The cells were triturated once with a glass Pasteur pipette in 1 ml of Neurobasal/B27 medium and subsequently twice by using a 1 ml insulin syringe with a 22 gauge needle. The cell suspension was passed through a 100 μm cell strainer and subsequently rinsed by 1 ml of Neurobasal/B27 medium. Cells were counted and adjusted to 50,000 cells per 60 μl.

Plating and Cultivatin of Cortical Cells 96-well plates were coated with 0.2 mg/ml Poly-L-Lysine and subsequently coated with 2μg/ml laminin in PBS, after which 60μl of cortical astrocyte-conditioned medium was added to each well. Subsequently, 60 μl of cortical cell suspension was added. The cells were cultivated in the presence of 10% $CO_2$ at 37° C. under 100% humidity. At day 1, there was a complete medium change (1:1-Neurobasal/B27 and astrocyte-conditioned medium) with addition of 1 μM cytosine-β-D-arabino-furanoside (mitosis inhibitor). On the second day, ⅔ of medium was changed. On day 5, ⅔ of the medium was changed again.

Cerebellar Microexplants from P8 Animals: Preparation, Cultivation and Fixation

The laminated cerebellar cortices of the two hemispheres were explanted from a P8 rat, cut into small pieces in PBS+0.65% D(+)glucose solution and triturated by a 23 gauge needle and subsequently pressed through a 125 μm pore size sieve. The microexplants that were obtained were centrifuged (60 g) twice (media exchange) into serum-free BSA-supplemented START V-medium (Biochrom). Finally, the microexplants were reconstituted in 1500 μl STARTV-medium (Biochrom). For cultivation, 40 μl of cell suspension was adhered for 3 hours on a Poly-D-Lysine (0.1 mg/ml) coated cover slip placed in 35 mm sized 6-well plates in the presence of 5% $CO_2$ under 100% humidity at 34° C. Subsequently, 1 ml of STARTV-medium was added together with the toxins and drugs. The cultures were monitored (evaluated) after 2–3 days of cultivation in the presence of 5% $CO_2$ under 100% humidity. For cell counting analysis, the cultures were fixed in rising concentrations of paraformaldehyde (0.4%, 1.2%, 3% and 4% for 3 min each) followed by a wash in PBS.

Toxin and Drug Administration for Cerebellar Cortical and Striatal Cells; Analysis All toxin and drug administration experiments were designed that 1/100 parts of okadaic acid (30 nM and 100 nM concentration and 0.5 mM 3-nitropropionic acid for cerebellar microexplants only), GPE (1 nM -1 mM) and G-2Methyl-PE (1 nM-1 mM) were used respectively at 8DIV for cortical cultures and 9DIV for striatal cultures. The incubation time was 24 hrs. The survival rate was determined by a colorimetric end-point MTT-assay at 595 nm in a multi-well plate reader. For the cerebellar microexplants four windows (field of 0.65 $mm^2$) with highest cell density were chosen and cells displaying neurite outgrowth were counted.

Results

The GPE analogue G-2Methyl-PE exhibited comparable neuroprotective capabilities within all three tested in vitro systems (FIGS. 12–15).

The cortical cultures responded to higher concentrations of GPE (FIG. 12) /or G-2Methyl-PE (10 μM, FIG. 13) with 64% and 59% neuroprotection, respectively.

Figure 14:
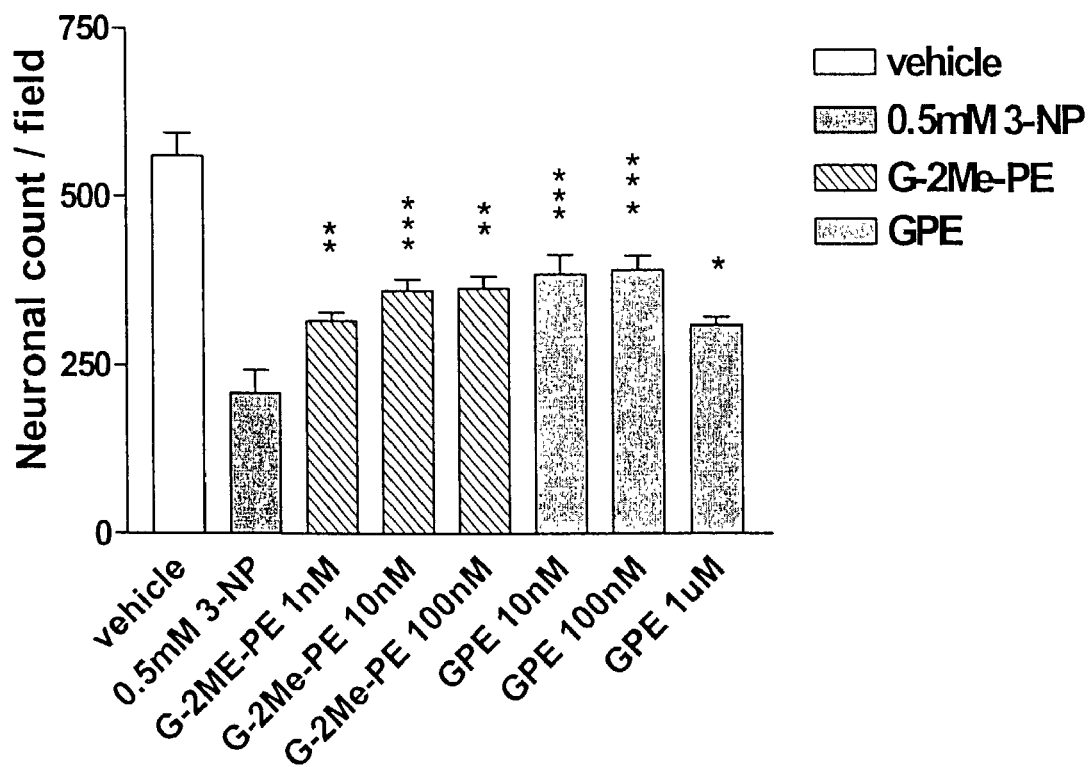
Figure 15:
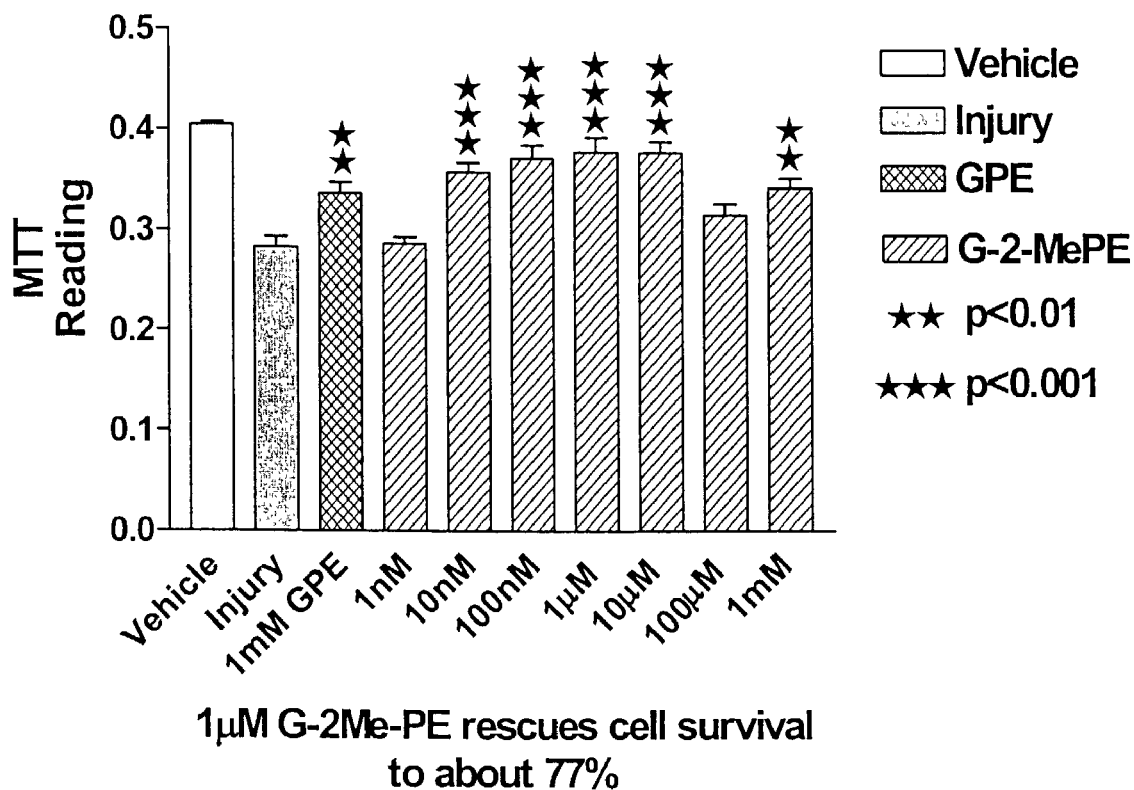

Whereas the other 2 types of cultures demonstrated neuroprotection at lower doses of G-2Methyl-PE (FIGS. 14 and 15). The striatal cells demonstrated neuroprotection within the range of 1 nM to 1 mM of G-2Methyl-PE (FIG. 15) while the postnatal cerebellar microexplants demonstrated neuroprotection with G-2Methyl-PE in the dose range between 1 nM and 100 nM (FIG. 14).

While this invention has been described in terms of certain preferred embodiments, it will be apparent to a person of ordinary skill in the art having regard to that knowledge and this disclosure that equivalents of the compounds of this invention may be prepared and administered for the conditions described in this application, and all such equivalents are intended to be included within the claims of this application.

What is claimed is:

1. A compound of Formula 1:

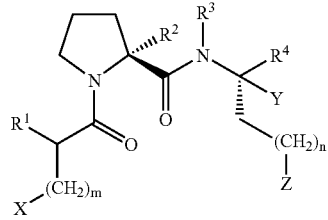

Formula 1 wherein: m=0; n=1; X=$NH_2$; Y=$CO_2H$; Z=$CO_2H$; $R^1$=$R^3$=$R^4$=H; and $R^2$=$CH_3$, or a salt thereof.

2. A pharmaceutical composition comprising the compound of claim 1, further comprising a pharmaceutically acceptable excipient.

3. The composition of claim 2, for oral administration, comprising a dosage form having an amount of said compound having a lower limit of about 1 mg/Kg and an upper limit of about 100 mg/Kg.

4. The composition of claim 3, wherein said dosage form further comprises a binder.

5. The composition of claim 2, wherein said compound is present in a an amount having a lower limit of about 0.0001 percent by weight; and an upper limit of about 10% by weight.

6. The composition of claim 2, wherein said compound is associated with a semi-permeable polymer matrix.

7. The composition of claim 6, wherein said semi-permeable polymer matrix is selected from the group consisting of polylactides, copolymers of L-glutamic acid and gamma-ethyl-L-glutamate, poly(2-hydroxyethyl methylacrylate), ethylene vinyl acetate, liposomes and poly-D-(−)-3-hydroxybutyric acid.

8. A capsule for oral administration comprising the compound of claim 1 and a pharmaceutically acceptable excipient.

9. A tablet containing the compound of claim 1 and a binder.

10. The composition of claim 2, wherein said pharmaceutically acceptable excipient is isotonic saline.

11. A method for treating neural degeneration, caused by hypoxia-ischemia or toxic injury comprising administering a pharmaceutical composition comprising a pharmacologically effective amount of the compound of claim 1 to a subject in need of such treatment.

12. The method of claim 11, wherein said effective amount is in the range having a lower limit of about 0.001 mg/Kg and an upper limit of about 1 gm/Kg.

13. The method of claim 11, wherein said composition is administered by an oral, topical, systemic, parenteral, subcutaneous, intravenous, intraspinal, intracisternal, intraventricular, implantation, infusion, or aerosol route.

14. The method of claim 11, wherein said hypoxia-ischemia or toxic injury is to the central nervous system.

15. The method of claim 11, wherein said hypoxia-ischemia or toxic injury is associated with degeneration of neurons of the central nervous system.

16. The method of claim 15, wherein said neurons are one or more of striatal, cerebellar or cortical neurons.

* * * * *

UNITED STATES PATENT AND TRADEMARK OFFICE
CERTIFICATE OF CORRECTION

PATENT NO.        : 7,041,314 B2                                      Page 1 of 1
APPLICATION NO.   : 10/155864
DATED             : May 9, 2006
INVENTOR(S)       : Norman A. Abood et al.

It is certified that error appears in the above-identified patent and that said Letters Patent is hereby corrected as shown below:

On the Title Page, (item 54) and in the Specification, Column 1, in the title, delete "PEPTIDOMINETICS" and add --PEPTIDOMIMETICS--.

Signed and Sealed this
Eighteenth Day of February, 2014

Michelle K. Lee
*Deputy Director of the United States Patent and Trademark Office*